United States Patent
Sakakura et al.

(10) Patent No.: US 7,119,227 B2
(45) Date of Patent: Oct. 10, 2006

(54) PROCESS FOR CATALYTIC VAPOR PHASE OXIDATION

(75) Inventors: Yasuyuki Sakakura, Mie (JP); Shuhei Yada, Mie (JP); Kimikatsu Jinno, Mie (JP); Hirochika Hosaka, Mie (JP); Yoshiro Suzuki, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 195 days.

(21) Appl. No.: 10/937,657

(22) Filed: Sep. 10, 2004

(65) Prior Publication Data

US 2005/0107483 A1    May 19, 2005

Related U.S. Application Data

(63) Continuation of application No. PCT/JP03/02855, filed on Mar. 11, 2003.

(30) Foreign Application Priority Data

Mar. 11, 2002   (JP)  .............................. 2002-064620

(51) Int. Cl.
*C07C 51/16*   (2006.01)
(52) U.S. Cl. ...................... 562/545; 562/532
(58) Field of Classification Search ................ 562/545, 562/532
See application file for complete search history.

(56) References Cited

U.S. PATENT DOCUMENTS 5,821,390 A * 10/1998 Ruppel et al. .............. 568/470
6,384,274 B1 * 5/2002 Elder et al. ................. 562/532
6,998,505 B1 * 2/2006 Yada et al. .................. 562/545
7,015,354 B1 * 3/2006 Petzoldt et al. ............. 562/547

FOREIGN PATENT DOCUMENTS

| CN | 1249300 A | 4/2000 |
| EP | 1 080 780 | 3/2001 |
| EP | 1 270 065 | 1/2003 |
| JP | 10-309457 | 11/1998 |
| WO | WO 01/42184 | 6/2001 |

* cited by examiner

*Primary Examiner*—Samuel A Barts
*Assistant Examiner*—Lalitha Nagubandi
(74) *Attorney, Agent, or Firm*—Oblon, Spivak, McClelland, Maier & Neustadt, P.C.

(57) ABSTRACT

The present invention provides a process for catalytic vapor phase oxidation which prevents runaway reaction or early deterioration of a catalyst, in the production of (meth)acrylic acid or the like from propylene or isobutylene by the catalytic vapor phase oxidation process using a multi-tubular reactor, which can lead to the production thereof constantly in high yield for a long period of time. Further, the present invention provides a process for catalytic vapor phase oxidation wherein raw material gas is introduced for oxidation into reaction tubes of a multi-tubular reactor which is equipped with, as arranged within the shell of the reactor, a plurality of reaction tubes having a catalyst packed therein and a plurality of baffle plates for changing the direction of the flow of a heating medium introduced into the shell, characterized in that the temperature of the catalyst packed in a reaction tube which is not connected with at least one baffle plate is measured at plural points in the direction of an axis of the reaction tube.

14 Claims, 4 Drawing Sheets

PROCESS FOR CATALYTIC VAPOR PHASE OXIDATION

CROSS REFERENCE TO RELATED APPLICATION

This is a Continuation Application of PCT Application No. PCT/JP03/02855, filed on Mar. 11, 2003, which was not published under PCT Article 21(2) in English. This application is based upon and claims the benefit of priority from the prior Japanese Patent Application No. 2002-064620, filed Mar. 11, 2002, the entire contents of which are incorporated herein by reference.

TECHNICAL FIELD

The present invention relates to a process for catalytic vapor phase oxidation which prevents a runaway reaction or early deterioration of a catalyst, in the production of (meth) acrylic acid or the like from propylene or isobutylene by the process for the catalytic vapor phase oxidation using a multi-tubular reactor, which makes the production in high yield constantly for a long period of time possible.

BACKGROUND ART

A usual multi-tubular reactor has a structure which is equipped with, as arranged within the shell of the reactor, a plurality of reaction tubes having a catalyst packed therein and a plurality of baffle plates having openings so as to distribute a heating medium introduced into the shell, entirely in the shell. It was common that the temperature of the heating medium flowing in the shell was measured, and on the basis of the result of the measurement, the operation control of the multi-tubular reactor was carried out while the temperature of the heating medium in the shell was uniformly controlled.

Most of reaction tubes disposed in the shell are connected with the baffle plates. However, some of reaction tubes passing through openings formed in the baffle plates are not connected with baffle plates. Catalyst layers in the reaction tubes, which are not in contact with the baffle plates, tend to have local heat accumulation spots (hot spots) formed due to the reaction heat. If such a hot spot was formed, the portion of the catalyst tended to be deteriorated due to an excessive heat generation, and the lifetime tended to decrease.

Further, in order to obtain proper performance in the lifetime of the catalyst by preventing formation of the hot spot, it was required to decrease the concentration of raw material gas introduced into the reaction tubes, or to limit the supply amount, whereby there was a case that (meth)acrylic acid or the like could not be produced constantly in high yield for a long period of time.

DISCLOSURE OF THE INVENTION

The present invention provides a process for catalytic vapor phase oxidation using a multi-tubular reactor, by which the above problems could be solved, and the summaries are follows.

(1) A process for catalytic vapor phase oxidation wherein raw material gas is introduced for oxidation into reaction tubes of a multi-tubular reactor which is equipped with, as arranged within the shell of the reactor, a plurality of reaction tubes having a catalyst packed therein and a plurality of baffle plates for changing the direction of the flow of a heating medium introduced into the shell, characterized in that the temperature of the catalyst packed in a reaction tube which is not connected with at least one baffle plate is measured.

(2) A process for catalytic vapor phase oxidation wherein raw material gas is introduced for oxidation into reaction tubes of a multi-tubular reactor which is equipped with, as arranged within the shell of the reactor, a plurality of reaction tubes having a catalyst packed therein and plurality of baffle plates for changing the direction of the flow of a heating medium introduced into the shell, characterized in that the temperature of the catalyst packed in a reaction tube which is not connected with at least one baffle plate, and the temperature of the catalyst packed in a reaction tube which is connected with all baffle plates, are measured.

(3) The process according to (1) or (2), wherein the temperature and flow rate of the heating medium to be introduced into the shell are controlled on the basis of the temperature of the catalyst measured.

(4) The process according to any one of (1) to (3), wherein the temperature of the catalyst is measured at 2 to 20 points in the direction of the axis of the reaction tube.

(5) The process according to any one of (1) to (4), wherein the temperature of the catalyst is measured by using a multipoint thermocouple.

(6) The process according to any one of (1) to (5), wherein the direction of the flow of the raw material gas, which flows in the reaction tubes, and the direction of a macroscopic flow of the heating medium which flows in the shell, are the same directions.

(7) The process according to any one of (1) to (6), wherein a plurality of catalyst layers, which have different activities, are packed in the reaction tubes.

(8) The process according to any one of (1) to (7), wherein the raw material gas contains propylene, isobutylene or (meth)acrolein, as a material to be oxidized.

EXPLANATION OF REFERENCE SYMBOLS 1a, 1b, 1c: Reaction tube
2: Shell of multi-tubular reactor
5a, 5b: Tube plate
6a, 6b: Baffle plate
9: Middle-tube plate
11: Thermometer for catalyst
14, 15: Thermometer for heating medium
Hm: Heating medium
Rg: Raw material gas

MODE FOR CARRYING OUT THE INVENTION

The process for catalytic vapor phase oxidation of the present invention will be described on the basis of the attached drawings.

The process for catalytic vapor phase oxidation of the present invention and a multi-tubular reactor to be used for the process for catalytic vapor phase oxidation will be described on the basis of FIG. 1.

Numeral 2 designates a shell for the multi-tubular reactor, in which reaction tubes 1a, 1b and 1c having a catalyst packed therein are secured by each of a lower tube plate 5b and an upper tube plate 5a.

At the top and bottom ends of the shell 2, inlet and outlet ports 4a and 4b for raw material gas Rg for reaction are provided, and the raw material gas Rg flows in the reaction tubes 1a, 1b and 1c in the direction of upward or downward flow. Such a flow direction is not particularly limited, but the upward flow is more preferred.

Further, a circular pipe 3a for introducing the heating medium Hm is provided on the outer periphery of the shell 2, and the heating medium Hm having a pressure increased by the circulation pump 7 is introduced into the shell 2 from the circular pipe 3a. The heating medium introduced into the shell 2 flows upward, while the flow direction is changed by the baffle plates 6a, 6b, and 6a as indicated by arrow marks. Meantime, the heating medium Hm absorbs heat of reaction by the contact with the outer surfaces of the reaction tubes 1a, 1b and 1c, and then is returned to the circulation pump 7 through the circular pipe 3b provided on the outer periphery of the shell 2.

A portion of the heating medium Hm which absorbs the heat of reaction, is fed into an exhaust pipe 8b provided at the upper part of the circulation pump 7 to be cooled by a heat exchanger (not shown), and then is sucked into the circulation pump 7 through a heating medium supply pipe 8a again to be introduced into the shell 2.

The temperature control for the heating medium Hm introduced into the shell 2 is carried out by controlling the temperature or flow volume of the heating medium to be flown from the heating medium supply pipe 8a. Further, the temperature of the heating medium Hm is measured by a thermometer 14 inserted in the inlet side of the circular pipe 3a.

Figure 4:
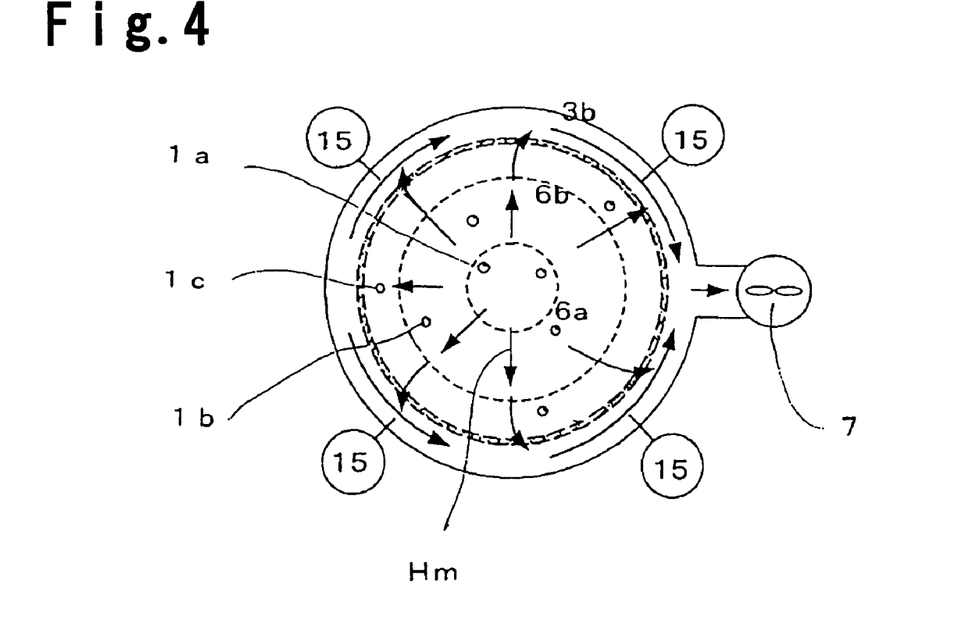
FIG. 4: View of the multi-tubular reactor of FIG. 1 observed from the above.

On each copper plate inside of the circular pipes 3a and 3b, a rectification plate (not shown) is provided in order to minimize circumferential distribution of the flow rate of the heating medium. As such a rectification plate, e.g. a poriferous plate or a plate having slits is employed. By changing the opening area of the poriferous plate or the distance of the slits, the heating medium Hm is rectified such that the heating medium can be introduced into the shell 2 from its entire periphery with a constant flow rate and a constant flow volume. Further, a plurality of thermometers 15 are arranged at even intervals in a circumferential direction as shown in FIG. 4, whereby the temperature in the circular pipe (3a, more preferably 3b in addition thereto) can be monitored.

In general, at least three baffle plates (6a, 6b and 6a) are usually disposed in the shell 2. Due to the presence of the baffle plates, the flow of the heating medium Hm in the shell 2 is such that it is firstly gathered from the peripheral portion to the center portion of the shell 2, and then is directed to the outer periphery as it flows upward through the opening portion of the baffle plate 6a to reach the inner wall of the shell 2.

Then, the flowing direction of the heating medium Hm is changed again, while the medium flows up through the space between the inner wall of the shell 2 and the outer periphery of the baffle plate 6b, and then is gathered to the center portion. Then, it flows up through the opening portion of the baffle plate 6a; flows along the lower surface of the upper-tube plate 5a in the shell 2 to head for the outer periphery; is introduced into the circular pipe 3b, and finally is sucked into the circulation pump 7 to be circulated in the shell 2 again.

Figure 2:
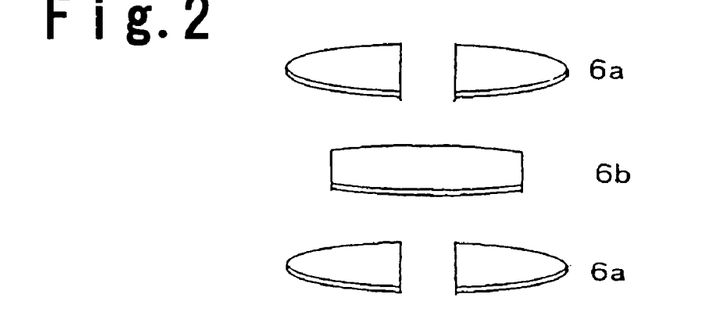
FIG. 2: Perspective view of an example of baffle plates equipped with a multi-tubular reactor.
Figure 3:
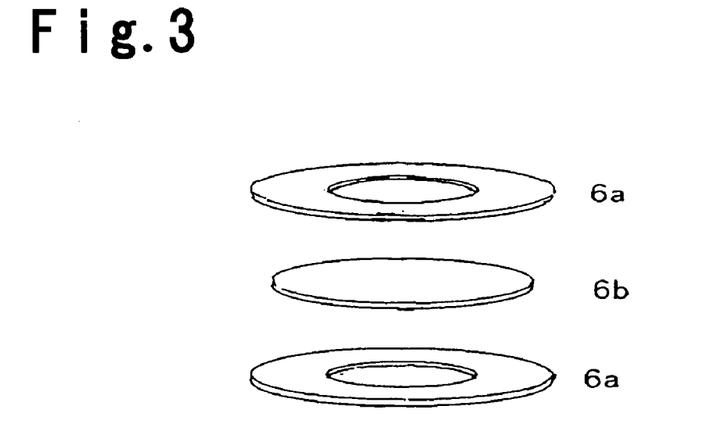
FIG. 3: Perspective view of another example of baffle plates equipped with a multi-tubular reactor.

As specific structures of the baffle plates to be used in the present invention, either waning circular baffle plates of segment type as shown in FIG. 2 or circular baffle plates as shown in FIG. 3 may be applied. Baffle plates of such types have no difference in the relation between the flow direction of the heat medium and the tube axes of the reaction tubes.

The baffle plates 6a have their outer periphery coincident with the inner wall of the shell 2, and have an opening portion near the center. Further, the diameter of the outer periphery of the baffle plate 6b is smaller than that of the inner wall of the shell 2, whereby a space is formed between the outer periphery of baffle plate 6b and the inner wall of the shell 2. The flow rate of the heating medium is changed by changing the direction of the flow, while the heating medium flows up through the respective opening portions and space.

A thermometer 11 is inserted in each of the reaction tubes 1a, 1b and 1c disposed in the shell 2, and the signals are transmitted to an external portion of the shell 2, whereby each temperature distribution in the direction of the tube axis, in the catalysts layers packed in the reaction tubes, is measured.

Multipoint type thermometers or thermometers 11 movable in a sheath to measure a plurality of points, are inserted in the reaction tubes 1a, 1b and 1c, whereby temperatures at 2 to 20 points in the direction of axes are measured.

The inner space of the shell 2 equipped with the reaction tubes 1a, 1b and 1c is divided by three baffle plates 6a, 6b and 6c, and divided spaces are classified into 3 types with respect to the flow direction of the heating medium Hm.

Namely, the reaction tube 1a is connected with the baffle plate 6b, whereby the flow direction of the heating medium Hm is restricted by only the baffle plate 6b, and the flow direction is not restricted by the other two baffle plates 6a since it passes through the opening portions of these baffle plates 6a.

Figure 1:
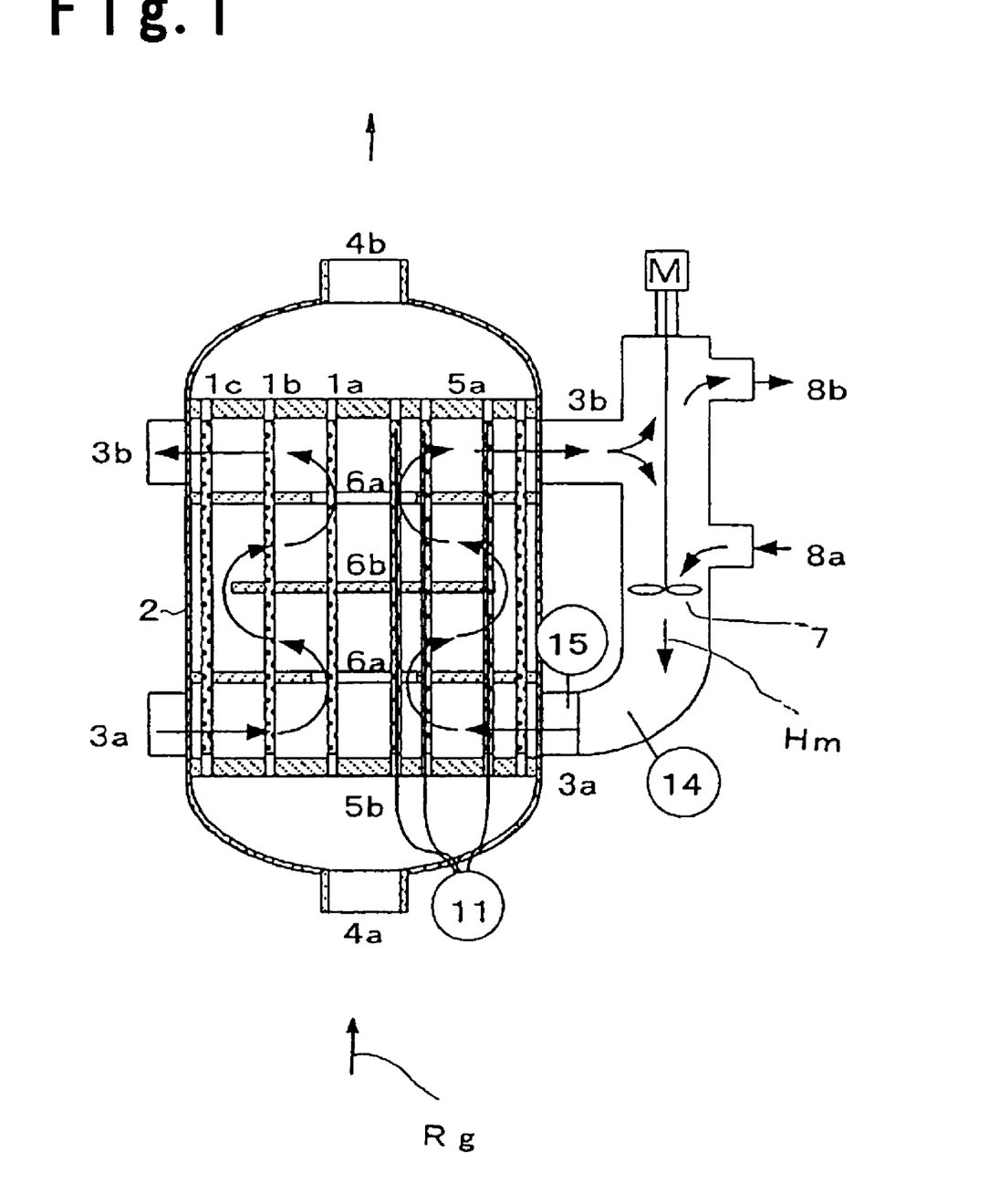
FIG. 1: Cross sectional view of an example of a multi-tubular reactor to be used for a process for catalytic vapor phase oxidation.

The heating medium Hm introduced from the circular pipe 3a into the shell 2 changes its flow direction at the center portion of the shell 2 as indicated by arrow marks in FIG. 1. Further, the reaction tube 1a is positioned so that the flow direction is changed, whereby the heating medium Hm flown around the outer periphery of the reaction tube 1a mainly flows parallel to the axis of the reaction tube 1a.

The reaction tube 1b is connected with three baffle plates 6a, 6b and 6a, whereby the flow direction of the heating medium Hm is restricted by the respective baffle plates. Further, the flow of the heating medium Hm flown around the outer periphery of the reaction tube 1b flows perpendicular to the axis of the reaction tube 1b at the approximately entire positions of the reaction tube 1b. Here, most of the reaction tubes disposed in the shell 2 are at positions corresponding to the reaction tube 1b.

Further, the reaction tube 1c passes through the space between the outer periphery of the reaction tube 6b and the inner wall of the shell 2 without any contact with the baffle plate 6b, whereby the flow of the heating medium Hm in the position is not restricted by the baffle plate 6b, and it flows parallel to the axis of the reaction tube 1c.

FIG. 4 shows the interrelation between the positional relation of the reaction tubes 1a, 1b and 1c and the baffle plates 6a, 6b and 6a and flows of the heating medium Hm.

When the opening portion of baffle plates 6a (the innermost circle of dotted line) is the gathering position of the heating medium Hm, that is, at the center of the shell 2, the heating medium Hm not merely flows parallel to the reaction tube 1a, but also hardly flows at the center of the opening portion of baffle plates 6a, i.e., the flow rate is approximately zero, whereby the heat conductivity efficiency is terribly bad. Therefore, there is a case that the reaction tube 1a is not disposed at such a position.

Figure 5:
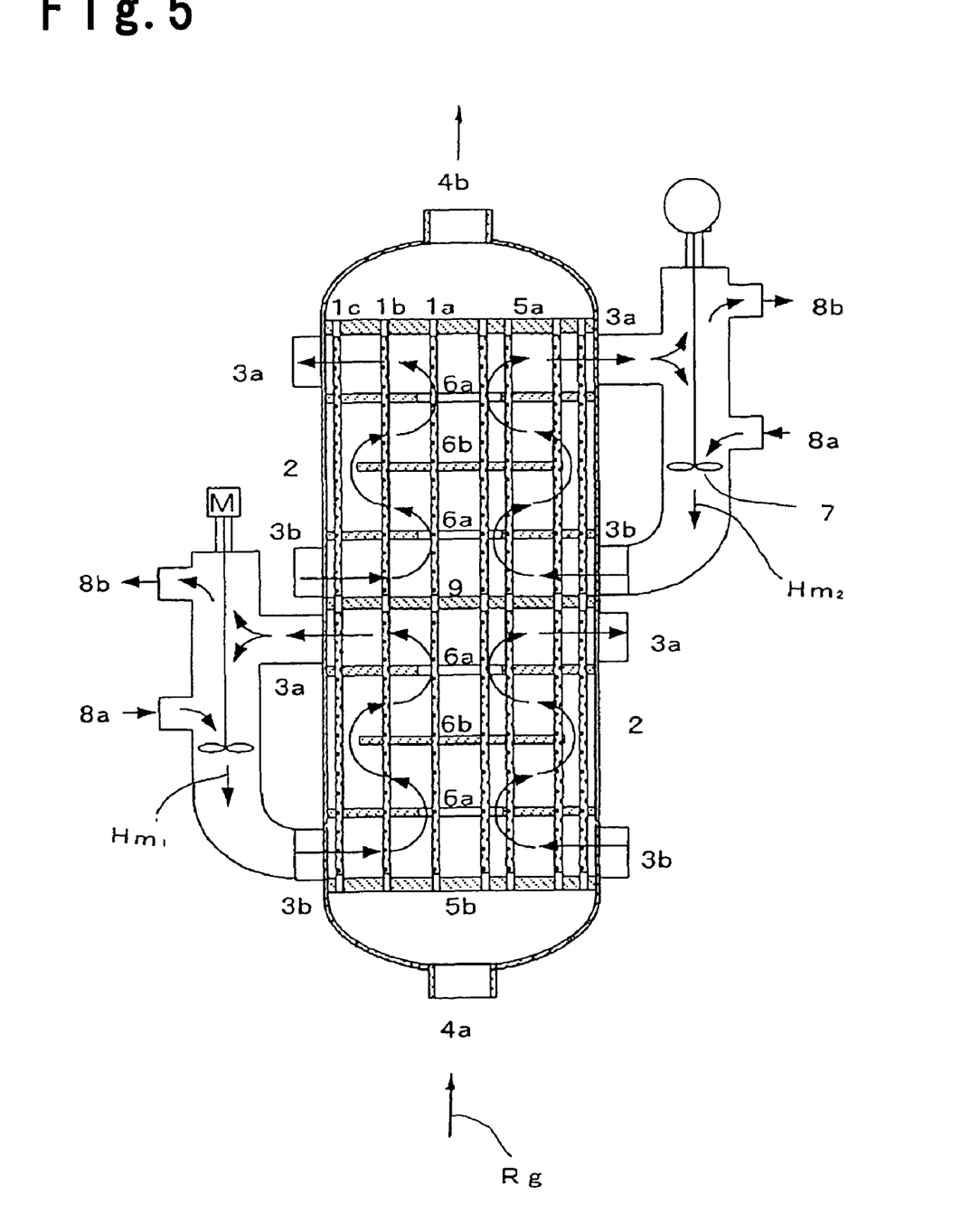
FIG. 5: Cross sectional view of another example of a multi-tubular reactor to be used for a process for catalytic vapor phase oxidation.

FIG. 5 is another example of the present invention in a case where the inner portion of the shell 2 of the reactor is divided by a middle-tube plate 9.

In divided spaces of the shell 2, heating media $Hm_1$ and $Hm_2$ are circulated respectively, and further, they are respectively subjected to temperature controls.

The upper and lower portions of the reaction tubes 1a, 1b and 1c, are partitioned by interposed layers of an inert material which are not involved in the reactions, different catalysts are respectively packed therein, and the temperatures of the respective catalysts are controlled under optimum conditions, to carry out reactions. Further, the position for interposing such an inert material is a portion corresponding to the positions where the outer peripheries of the reaction tubes 1a, 1b and 1c are in contact with middle-tube plate 9.

Raw material gas Rg is introduced from an inlet 4a of raw material gas into the shell 2, and then reactions are sequentially carried out as the gas flows in the reaction tubes 1a, 1b and 1c to produce a product.

For example, propylene or isobutylene is introduced as a gas mixed with molecular oxygen-containing gas, then converted to (meth)acrolein at the lower portion, and then oxidized in the upper portion to form (meth)acrylic acid.

Figure 6:
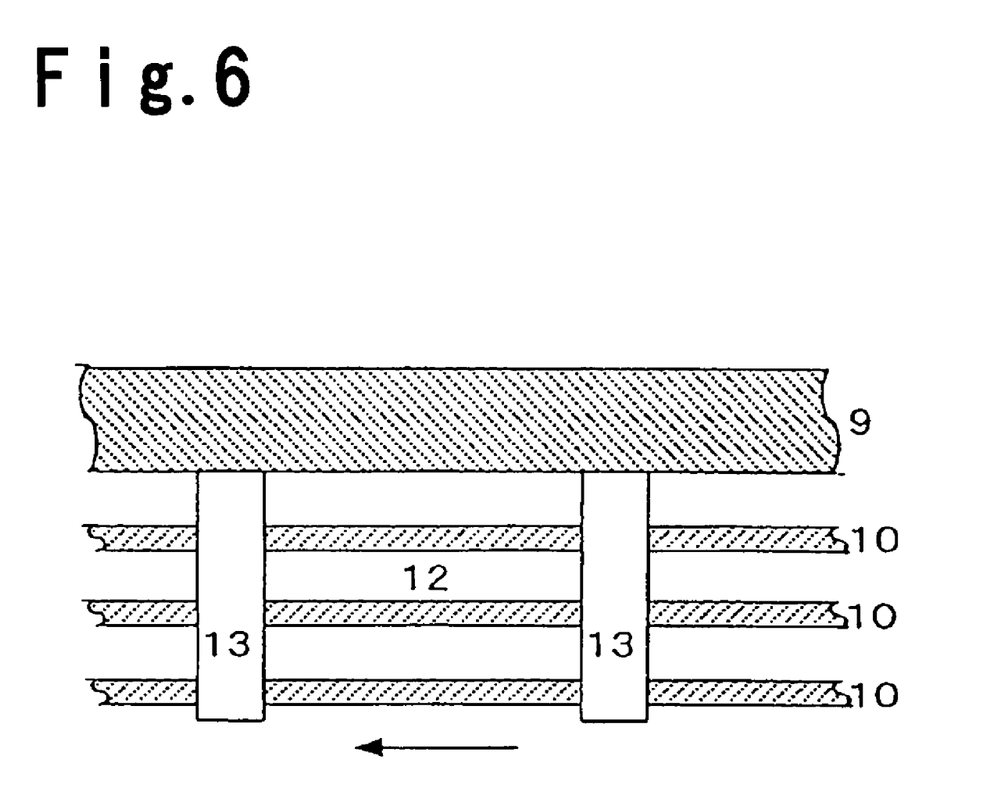
FIG. 6: Partial sectional view of a middle-tube plate and heat-shielding plates equipped with the multi-tubular reactor of FIG. 5.

In FIG. 6, numeral 9 designates a middle-tube plate, three heat shields 10 are fixed at positions below the lower surface of the middle-tube plate 9 by means of spacer rods 13. Two or three heat shields 10 are provided below the middle-tube plate 9, as shown in this figure, or above thereof at positions as well as being not more than 100 mm, whereby stagnation spaces 12 having no flow are formed even though the heating medium $Hm_1$ or $Hm_2$ is filled. Accordingly, it is preferred to let the spaces have a heat-insulating effect.

The reasons why the heat shields 10 are attached to the middle-tube plate 9 are as follows. That is, in FIG. 5, in a case where the controlled temperature difference between the heating medium $Hm_1$ introduced into the lower portion in the shell 2 and the heating medium $Hm_2$ introduced into the upper portion exceeds 100° C., it is not allowed to disregard a heat transfer from a hot-temperature medium to a low-temperature medium, whereby the accuracy of the control of the reaction temperature of the catalyst at a low-temperature side is deteriorated. In such a case, it is required to provide heat insulation for the prevention of the heat transfer above and/or below the middle-tube plate 9.

Into the multi-tubular reactor to be used for catalytic vapor phase oxidation, a mixed gas is introduced as the raw material gas Rg of reactions, wherein the mixed gas comprises propylene or isobutylene, and/or (meth)acrolein mixed with molecular oxygen-containing gas or steam.

The concentration of propylene or isobutylene is from 3 to 10 vol %, and oxygen is from 1.5 to 2.5 (molar ratio) and steam is from 0.8 to 2 (molar ratio) to propylene or isobutylene.

The raw material gas Rg introduced therein, is divided by the respective reaction tubes 1a, 1b and 1c, and then, as it flows in the reaction tubes, reacted by an oxidation catalyst contained therein. However, distribution of the raw material gas Rg to the respective reaction tubes is affected by e.g. the packing amounts or the packing densities of the catalyst in the reaction tubes. Such packing amounts or packing densities of the catalyst are determined at the time of packing operation of the catalyst in the reaction tubes. Therefore, it is very important to pack the catalyst uniformly in the respective reaction tubes.

In order to pack the catalyst uniformly, it is possible to employ a method of making the packing density constant by making the weight of the catalyst packed in the respective reaction tubes uniform, or by adjusting the time for packing the catalyst to be the same.

The raw material gas Rg, which flows in the respective reaction tubes 1a, 1b and 1c, is firstly heated during flowing through the inert agent layer packed in each inlet part, to reach the reaction starting temperature.

The raw material (propylene or isobutylene) is oxidized by the catalyst contained as the next layer in each reaction tube, and the temperature is further increased by the heat of reaction.

The reaction amount is largest at the inlet part of the catalyst layer, and if it exceeds the heat removal amount by the heating medium Hm, the heat of reaction generated will serve to increase the temperature, whereby a hot spot may be formed. The hot spot is likely to be formed at a position of from 300 to 1000 mm from the inlets of the reaction tubes 1a, 1b and 1c.

Accordingly, the heat removal effect by the flow of the heating medium Hm, is most important within 1,000 mm from the inlets of the reaction tubes 1a, 1b and 1c. If the amount of the heat of reaction generated here exceeds the heat removal ability of the heating medium Hm from the periphery of the reaction tubes, the temperature of the raw material gas Rg will further rise, whereby the generation amount of the heat of reaction will further increase, and finally, a runaway reaction will take place. Thus, it is possible that the temperature of the catalyst exceeds the maximum allowance, and the catalyst undergoes a quality change, whereby its deterioration or breaking can occur.

With respect to the preliminary-step reactor for producing acrolein by the oxidation reaction of propylene with the molecular oxygen-containing gas, as an example, the temperature of the heating medium Hm is from 250 to 350° C., and the maximum allowable temperature against the hot spot is from 400 to 500° C.

Further, with respect to the subsequent step reactor for obtaining acrylic acid by oxidizing acrolein with the molecular oxygen-containing gas, the temperature of the heating medium Hm is from 200 to 300° C., and the maximum allowable temperature against the hot spot is from 300 to 400° C.

As the heating medium Hm which flows in the shell 2 i.e., around outer peripheries of the reaction tubes 1a, 1b and 1c, Niter which is a mixture of nitrates, is widely used, but a phenyl ether heating medium of an organic liquid system may also be used.

The heat removal is carried out at the outer peripheries of the reaction tubes 1a, 1b and 1c, during the flow of the heating medium Hm. However, with respect to the heating medium Hm introduced from the circular pipe 3a to the shell 2, a position where the medium flows from the outer periphery of the shell 2 to the center portion, and a position where the flow direction is turned around at the center portion, are present, and it was found that the heat removal effect is extremely different in the respective positions.

When the flow direction of the heating medium Hm is perpendicular to the tube axis of the reaction tube, the heat transfer coefficient is from 1,000 to 2,000 W/m²° C. However, when the flow direction is not perpendicular thereto, it is different in accordance with the flow rate or the difference of upward flow or downward flow. However, even if Niter is used as a heating medium, the heat transfer coefficient is usually from 100 to 300 W/m²° C. at the utmost.

On the other hand, the heat transfer coefficient of the catalyst layers in the reaction tubes 1a, 1b and 1c, of course, relies on the flow rate of the raw material gas Rg. However, it is approximately 100 W/m²° C., whereby, obviously, it is not changed from a conventional knowledge that the rate controlling of the heat transfer is the gas phase in the tubes.

Specifically, when the flow of the heating medium Hm is perpendicular to the tube axes of the reaction tubes 1a, 1b and 1c, the heat transfer resistance of the outer periphery of the tube is from 1/10 to 1/20 to that of the reaction tube gas Rg side. Even if the flow rate of the heating medium Hm side is changed, such a change will not substantially affect the overall heat transfer resistance.

However, when Niter flows parallel to the axes of the tubes, the heat transfer coefficients of inside and outside of the reaction tubes 1a, 1b and 1c are nearly equal, whereby the influence of the flow state at the outer periphery of the tubes on the heat removal efficiency is substantial. Namely, when the heat transfer resistance of the outer periphery of the tube is 100 W/m²° C., the overall heat transfer coefficient becomes half thereof, and further, half of the change in the heat transfer resistance of the outer periphery of the tube is influential over the overall heat transfer coefficient.

It is required to monitor the difference of the heat transfer coefficients carefully when the reaction is practically carried out.

The reaction tube 1b is one restricted by all baffle plates (usually three sheets), wherein the overall heat transfer coefficient is large, the maximum temperature is low in the temperature distribution in the direction of the tube axis of the catalyst layer in the reaction tube, and it is considered to be average in the entire shell 2.

Further, the reaction tube which is provided at a position where the heating medium Hm changes the direction, is the reaction tube 1c unrestricted by one baffle plate, or the reaction tube 1a unrestricted by two baffle plates.

When the supply amount of the raw material gas Rg to the reaction tubes 1a, 1b and 1c is increased, or the reaction temperature is maintained to be high to obtain a high conversion, the maximum temperature of the reaction tubes tends to increase to form hot spots, whereby the possibility of the deterioration of the catalyst or the runaway reaction will increase.

In such a case, it is necessary to strictly control the temperature of the heating medium Hm. A plurality of thermometers 11 are inserted in a plurality of the reaction tubes 1a or 1c, and the temperature of the heating medium Hm is controlled, while monitoring the hot spot temperatures of the respective reaction tubes. The temperature of the heating medium Hm is thus strictly controlled to a proper temperature, whereby the desired reaction result can be obtained, and further, e.g. deterioration of the catalyst can be prevented, and it becomes possible that the continuous operation can be carried out for a long period of time.

When the maximum temperature of the reaction tube 1a is close to the restricted temperature, the temperature of the heating medium Hm may be lowered. However, in the case of the reaction tube 1c, there may be a case where the temperature at the downstream portion to the position showing the maximum temperature will increase. Therefore it is not allowed to neglect the monitoring.

When the conversion by the reaction is lower than the proper value, it is necessary to raise the temperature of the heating medium Hm. However, even in such a time, it is important to monitor the maximum temperature of the reaction tube so that it will not exceed the restricted temperature. Further, the maximum temperature of the reaction tube, or the position showing the maximum temperature of the reaction tube, may sometimes change, also when the supply amount to the shell 2 of the raw material gas, as mixed gas of propylene or isobutylene with molecular oxygen-containing gas or the like, increases or decreases.

Further, it is more preferred that thermometers 11 are inserted also in a plurality of reaction tubes 1b, and the temperature of the heating medium Hm be controlled while monitoring the temperatures of the catalyst layers in the reaction tubes.

The maximum temperature of the reaction tubes 1b, which occupy the great majority of the reaction tubes, is measured and compared with the maximum temperature of the reaction tubes 1a or 1c in other areas, whereby it is possible to bring the reaction result to be more proper.

The difference in the maximum average temperature (the average value in the maximum temperature per every reaction tube) of the reaction tubes present in the respective areas is preferably within 30° C., particularly preferably within 20° C., more preferably within 15° C. If the difference is too large, the reaction yield tends to decrease, such being undesirable.

The number of the reaction tubes 1a, 1b and 1c having thermometers 11 inserted, in the respective areas, is at least 1, preferably from 3 to 5. If the inserted number is a few, there may be a case where abnormality in the maximum temperature of the reaction tubes can not be detected, even if there is a temperature unevenness of the heating medium Hm introduced into the circular pipe 3a of the shell 2.

Further, the above area is meant for aggregation of reaction tubes which extend through an opening or space of the same baffle plate, and further are connected to and supported by the same baffle plate.

The types of the baffle plates for the purpose of shifting the flow direction of the heating medium Hm flowing in the shell 2 or of preventing a bypass flow of the heating medium Hm, are not particularly restricted. However, a segment baffle plate or a circular baffle plate as shown in FIG. 2 or 3 is employed, and particularly, the circular baffle plate seems to be widely used.

The area of the opening at the center of the baffle plate 6a is from 5 to 50%, preferably from 10 to 30% of the inner cross sectional area of the shell 2.

The space area formed by the outer periphery of the baffle plate 6b and the inner wall of the shell 2 is from 5 to 50%, preferably from 10 to 30% of the inner cross sectional area of the shell 2.

If the opening ratio and the space ratio of the baffle plates 6a and 6b are too small, the flow path of the heating medium Hm will be long, the pressure loss between the circular pipes 3a and 3b will increase, and the power of the circulation pump 7 will increase. On the other hand, if the ratios are too large, the number of the reaction tubes 1a and 1c will increase.

The spacing of the respective baffle plates (the distance between the baffle plates 6a and 6b; the distance between the baffle plate 6a and the upper-tube plate 5a; and the distance between the baffle plate 6a and the lower-tube plate 5b) is usually set to be an equal interval. However it may not necessarily be set to be an equal interval so long as the required flow rate of the heating medium Hm determined by the heat of oxidation reaction generated in the reaction tube can be secured, and the pressure loss of the heating medium can be made to be low.

It is necessary to avoid that the position of the maximum temperature in the temperature distribution in the reaction tubes 1a, 1b or 1c be the same as the position of the baffle plate 6a, 6b or 6a. Near the surface of each baffle plate, the flow rate of the heating medium decreases and the heat transfer coefficient will be low. Accordingly, if the position of the maximum temperature of the reaction tube is overlapped therewith, it becomes highly likely that the hot spot is formed.

In the shell 2, inside of the reaction tubes 1a, 1b and 1c containing the oxidation catalyst is a gas phase, and further, the maximum linear velocity of the raw material gas is restricted by the catalyst, whereby the heat transfer coefficient in the respective reaction tubes will be low, and it becomes a heat-transfer rate-controlling process. Accordingly, the inner diameters of the reaction tubes are very important.

The inner diameters of the reaction tubes 1a, 1b and 1c are affected by the amount of the heat of reaction and the particle diameter of the catalyst in the tubes. However, an inner diameter of from 10 to 50 mmΦ is usually selected. It is more preferably from 20 to 30 mmΦ. If the inner diameters of the respective reaction tubes are too small, the weight of the catalyst packed therein will decrease, and the number of the reaction tubes will be large to the required catalytic amount, whereby the shell 2 will be large.

On the other hand, if the inner diameters of the reaction tubes are too large, the contact of the catalyst and the surface area of the reaction tube will be small to the required heat removal amount, whereby heat transfer efficiency for heat removal of the heat of reaction will decrease.

As the thermometer 11 inserted into the reaction tube, usually, one having a columned shape, in which a plurality of thermocouples, resistance temperature sensors or the like are covered with an outer tube (thermowell), or one in which a thermocouple is movable in the sheath, may be used.

It is necessary that the thermometer 11 is set at a position on the tube axis, and projections are provided on the surface of the outer tube, whereby the distance from the inner wall of the reaction tube is restricted to overlap with the position of the tube axis.

It is preferred that the tube axis of the reaction tube and the central axis of thermometer 11 are overlapped. Further, it is preferred that the projections, which are formed on the thermometer 11, are provided in front and rear of the position of the maximum temperature in the catalyst layer.

As the outer tube (thermowell) of thermometer 11, one having a diameter of at most 15 mmΦ is used. Also, in consideration of the relation to the inner diameter of the reaction tube, the distance to the inner wall of the reaction tubes should be at least two times of the particle diameter of the catalyst. If the particle diameter of the catalyst is 5 mm and the inner diameter of the reaction tube is 30 mmΦ, the diameter of the outer tube of thermometer 11 will be required to be at most 10 mmΦ.

If the packing density of the catalyst is different between the reaction tube having a thermometer 11 inserted and other reaction tube, the accurate temperature can not be measured. Accordingly, the outer diameter of thermometer 11 is preferably at most 6 mmΦ, more preferably from 2 to 4 mmΦ.

The present invention is basically to take measures to meet the situation by analyzing the flow rate and the heat transfer coefficient of the heating medium Hm, and focusing on the presence of a portion having a low heat transfer coefficient, in the respective portions in cross section of the shall 2. However, with respect to the reaction tube disposed at the portion having a low heat transfer coefficient, particularly, with respect to the reaction tube 1a and a reaction tube in the vicinity thereof, an area having an extremely low heat transfer coefficient is found in the opening portion of the baffle plate (the round portion at the center in the circular baffle plate) at the center or in the vicinity thereof, in cross section of the shell 2. Such an area is found at or near the center of the opening portion of the baffle plate 6a. Therefore, it is recommended that no reaction tube be provided at such an area corresponding to a portion having a cross-sectional area ratio of the shell of from 0.5 to 5%. If such a portion is smaller than 0.5%, it is required to set the flow amount of the heating medium Hm to be at least two times so that the heat transfer coefficient be at least the minimum of the required value, whereby the power of the circulation pump 7 will have to be increased.

However, if the area where no reaction tube be provided is more than 5%, the waist diameter of the shell 2 will have to be increased in order to provide the required number of reaction tubes.

With respect to the reaction tubes 1a which are not supported by the baffle plate 6a, it is preferred not to provide them from 30 to 80% of the width of the opening portion of the baffle plate 6a (in the case of the segment baffle plate of FIG. 2) or of the diameter of the opening portion of the baffle plate 6a (in the case of the circular baffle plate of FIG. 3).

In FIGS. 1 to 5, the upward flow direction of the heating medium Hm in the shell 2 is indicated by arrow marks. However, the present invention can be applied also to a case where the flow direction is opposite.

When the direction of the circulation flow of the heating medium Hm is to be determined, it is necessary to take due care to avoid a phenomenon that the gas which may stay in the upper portions of the shell 2 and the circulation pump 7, particularly the inert gas such as nitrogen, will be included in the flow of the heating medium.

In a case where the heating medium Hm is the upward flow as shown in FIG. 1, if the gas is included at the upper portion of the circulation pump 7, the cavitation phenomenon may be observed in the circulation pump, and in the worst case, the pump may be damaged. In the opposite case, the phenomenon of inclusion of the gas will occur also at the upper portion of the shell 2, and the retention portion of the gas phase will be formed at the upper portion of the shell 2, whereby the upper portion of the reaction tubes corresponding to the gas retention portion will not be cooled by the heating medium Hm.

As measures for preventing the gas from staying, it is necessary to set a gas venting line for substitution of the gas in the gas layer with the heating medium Hm. For that purpose, the heating medium pressure of the supply-pipe of the heating medium 8a should be increased, and the exhaust pipe of the heating medium 8b be provided at an upper portion as far as possible to increase the pressure in the shell 2. The exhaust pipe of the heating medium 8b should be provided at a higher position than the upper-tube plate 5a.

The flow direction of the raw material gas Rg in the reaction tubes 1a, 1b and 1c may be upward or downward. However, a parallel flow is preferred in relation to the heating medium flow.

The heating values in the reaction tubes 1a, 1b and 1c are the largest at the inlet ports, and the formation position of the hot spot is often found at a position on the tube axis of the reaction tube in a range of from 300 to 1,000 mm from the inlet.

In connection with the baffle plates, the position of the hot spot is often found in an area between the upper-tube plate 5a or the lower-tube plate 5b and the baffle plate 6a. By supplying the heating medium Hm having a controlled temperature directly to the positions of the tube axes of the reaction tubes 1a, 1b and 1c corresponding to the maximum temperature of the reaction tubes, the formation of the hot spot can readily be controlled. Accordingly, it is preferred that the macroscopic direction of the flow of the heating medium Hm and the flow direction of the raw material gas Rg are the same direction, namely, the parallel flow.

The heat transfer amount, namely the reaction heat amount can be calculated by the heat transfer coefficient×heat transfer area×(catalyst layer temperature−heating medium temperature). Accordingly, a method of lowering the reaction heat amount per the surface area (the heat transfer area) of the reaction tube is effective to lower the maximum temperature of the reaction tube.

In order to equalize the heating value of the heat of reaction, at least two types of catalyst layers having different activities are packed in the same reaction tube. It is preferred that a catalyst layer having a lower activity is packed at the inlet side, and a plurality of catalyst layers are packed in the reaction tube so that the catalyst layer is changed over to one having a higher activity in the flow after the peak of the temperature distribution.

As a method for controlling the activity of the catalyst layer, a method of using a catalyst having a different activity by controlling the composition of the catalyst or a method of controlling the activity by mixing catalyst particles with inert particles to dilute the catalyst may, for example, be mentioned.

A catalyst layer having a high proportion of inert particles (the proportion of the catalyst particles in the mixed particles: dilution rate) is packed in the inlet parts of the reaction tubes 1a, 1b and 1c, and a catalyst layer having a low or zero dilution rate is packed in the later flow of the reaction tube. The dilution rate is different depending on the catalyst. However, the dilution rate in the earlier stage is from 0.3 to 0.7 in many cases. The dilution rate in the later stage of from 0.5 to 1.0 is preferably used. As the activity change or the dilution of the catalyst, two or three stages are usually applied.

The dilution rate of the catalyst packed in the reaction tubes 1a, 1b and 1c is not required to be equal with respect to all tubes. For example, the maximum temperature of the reaction tube 1a is high, whereby the possibility of the deterioration of the catalyst is high. In order to avoid such deterioration, it is possible to decrease the dilution rate at the earlier stage, and on the contrary, to increase the dilution rate at the later stage.

If the conversions in the reactions of the respective reaction tubes are different, the average conversion or the yield in the entire reactor will be thereby affected. Therefore, it is preferred that the respective reaction tubes be set to obtain the same conversion even if the dilution rate is changed.

The present invention is suitably applied to a multi-tubular reactor for oxidizing propylene or isobutylene by molecular oxygen-containing gas, or a multi-tubular reactor for oxidizing (meth)acrolein by molecular oxygen-containing gas to obtain (meth)acrylic acid. As a catalyst to be used for the oxidation of propylene, a multi-component composite metal oxide composed mainly of Mo—Bi type is preferably used, and as a catalyst for producing acrylic acid by oxidizing acrolein, a composite oxide composed mainly of Mo—V type is preferably used.

Propylene or isobutylene is oxidized by two steps, whereby it is possible to use two multi-tubular reactors, and different catalysts may be packed in the respective reactors. As shown in FIG. 5, however, the present invention can be applied to a case where the shell side of one reactor is divided into at least two compartments by a middle-tube plate, and then different catalysts may be packed therein respectively to obtain (meth)acrylic acid in one reactor.

EXAMPLES

Example 1

For carrying out the oxidation reaction of propylene, as catalyst (A), a catalyst having a composition (atomic ratio) of Mo=12, Bi=5, Ni=3, Co=2, Fe=0.4, Na=0.2, B=0.4, K=0.1, Si=24 and O=x, (the composition of oxide x is a value determined by oxidation states of the respective metals; the same applies hereinafter), and further, as catalyst (B), a catalyst having a composition (atomic ratio) of Mo=35, V=7, Sb=100, Ni=43, Nb=3, Cu=9, Si=20 and O=x, were respectively produced in accordance with usual methods to obtain catalyst powders. The catalyst powders were respectively molded to form ring shape catalysts having a outer diameter=5 mmΦ, an inner diameter=2 mmΦ and a height=4 mm and used. A multi-tubular reactor with an inner diameter of the shell=3,500 mmΦ having 9,000 reaction tubes made of stainless steel, as shown in FIG. 1, was used, wherein the reaction tubes had a length=3,500 mm, an inner diameter=24 mmΦ and an outer diameter=28 mmΦ respectively. The reaction tubes were not arranged in the round-shaped portion with the diameter of the center portion=500 m in the shell.

The baffle plates were provided at equal intervals in the order of the circular baffle plates 6a-6b-6a, and the respective opening ratios of the baffle plates were 18%. Further, the baffle plates 6a had diameters of opening portion=1,480 mmΦ, and the baffle plate 6b had the inner diameter=3,170 mmΦ.

Further, as disposed in the shell in FIG. 1, the number of the reaction tubes 1a was 1,534, that of the reaction tubes 1c was 1,740 and the rest was the reaction tubes 1b.

As the heating medium Hm, a molten salt Niter being a mixture of nitrates was used, and it was supplied from the lower side of the shell 2.

As the reaction temperature, the temperature of Niter to be supplied to the shell 2, measured by thermometer 14, was used. Further, the flow rate of Niter was controlled such that the temperature difference between the outlet and inlet of the shell 2 was 4° C.

To the respective reaction tubes, 1.5 L of the catalyst (A) was packed, raw material gas Rg with a propylene concentration of 9 vol % was supplied from a lower portion of the reactor at a gage pressure of 75 kPa.

To the reaction tubes 1a, 1b and 1c, thermometers 11 having 10 measurement points in the direction of each tube axis, were inserted to measure the temperature distribution. In each area of the reaction tubes 1a, 1b and 1c, two thermometers (six in total) are inserted.

In order to detect the maximum temperatures of the respective reaction tubes accurately, the measurement points of thermometers 11 were provided respectively at 250 mm intervals of from the inlet port of the reaction tubes to the position of 1,500 mm, and at 400 mm intervals in the position beyond 1,500 mm. The maximum temperatures of the tubes were recorded by using such thermometers 11.

When the temperature of the heating medium Hm was set to be 331° C., the average values of the maximum temperatures of the respective reaction tubes were 410° C. in the reaction tubes 1a, 390° C. in the reaction tubes 1b and 390° C. in the reaction tubes 1c. Further, in such a case, it was found that the propylene conversion was 97%, and the yield was 92%.

Example 2

By using the same reactor as in Example 1, molecular oxygen-containing gas (oxygen concentration: 15 vol %) was supplied at a ratio of 35 vol % and reacted to the outlet gas of the reactor in Example 1, to produce acrylic acid.

In the respective reaction tubes, 1.2 L of the catalyst (B) was packed. Further, the reaction was carried out in the same manner as in Example 1 except that the temperature of the heating medium Hm was adjusted to 275° C.

The average values of the maximum temperatures of the respective reaction tubes were 330° C. in the reaction tube 1a, 300° C. in the reaction tubes 1b and 300° C. in the reaction tubes 1c. Further, in such a case, it was found that the conversion of the reaction was 99%, and the yield was 90.5% by calculation on the basis of propylene.

Example 3

The same reactor as in Example 1 was used, and the catalyst (A) and ring inert obtained by molding an inert material (alumina), were mixed at 1:1 and packed in the reaction tubes from their inlets to the position of 1,500 mm. In the rest of 1,800 mm in the reaction tubes, only the catalyst (A) was packed, and in the residual 200 mm, aluminum balls inert to the present reaction were packed.

Further, the reaction was carried out in the same manner as in Example 1 except that the temperature of the heating medium Hm was adjusted to 335° C. As thermometers to be used for measurement of the catalyst layers in the reaction tubes, ones having 15 measurement points were used, and the measurement was carried out at 200 mm intervals.

The temperature distribution of the respective catalyst layers was measured, and it was found that the catalyst layers had two maximum temperatures.

When they are shown as the primary maximum temperature and the secondary maximum temperature from the inlets of the reaction tubes, as for the respective average values, in the reaction tubes 1a, the primary maximum temperature was 393° C. and the secondary maximum temperature was 345° C., in the reaction tubes 1b, the primary maximum temperature was 370° C. and the secondary maximum temperature was 350° C., and in the reaction tubes 1c, the primary maximum temperature was 365° C. and the secondary maximum temperature was 380° C.

In comparison with a case where the catalyst was not diluted, the temperature of the heating medium Hm was higher by 4° C. However, the respective maximum temperatures in the catalyst layers were lower by from 10 to 20° C., even when the higher ones were compared. Thus, the result shows that an extension in the lifetime of the catalyst and constant operation can be expected.

Further, the total yield of acrolein and acrylic acid obtained from propylene was found to be 92.5%.

Comparative Example 1

The reaction was carried out in the same manner as in Example 2 except that thermometers were not inserted in the reaction tubes 1a and 1c, but the same thermometers as in Example 1 were inserted in the reaction tubes 1b connected to all baffle plates and having a good heat removal efficiency.

In order to bring the conversion of acrolein to be from 99% to 99.5%, the inlet temperature of the heating medium Hm was changed from 275 to 280° C., whereby the maximum value in the distribution of the temperature of the catalyst layers in the reaction tubes 1b became 310° C.

By analyzing the reaction product gas, the conversion of acrolein was measured, whereby the conversion rate was found as decreased to 97.9%. After that, the operation was continued, whereby the conversion gradually decreased. Therefore, the inlet temperature of the heating medium Hm was further raised by 2° C. to 282° C., whereby the conversion of acrolein further decreased.

When the conversion of acrolein decreased to 95%, the reaction was suspended to check the catalyst in the reaction tubes. No abnormality was observed in the catalyst in the reaction tubes 1b and 1c. However, among the reaction tubes 1a, particularly the catalyst in approximately 350 reaction tubes 1a disposed in the vicinity of the center of the reactor, was found to have been remarkably deteriorated and changed in the shape and have lost its catalytic activity. The catalyst was presumably exposed to a high temperature of at least 400° C.

INDUSTRIAL APPLICABILITY

In a process for catalytic vapor phase oxidation employing a multi-tubular reactor, according to the present invention, the inside temperature of the reaction tubes having a catalyst packed, disposed in the shell of the reactor, is measured and on the basis of this temperature, the temperature and flow rate of a heating medium introduced in the shell are controlled, whereby in the production of (meth) acrylic acid or the like from propylene or isobutylene, a runaway reaction or early deterioration of the catalyst can be prevented, and it becomes possible to produce it constantly in high yield for a long period of time.

The entire disclosure of Japanese Patent Application No. 2002-064620 filed on Mar. 11, 2002 including specification, claims, drawings and summary is incorporated herein by reference in its entirety.

What is claimed is:

1. A process for catalytic vapor phase oxidation wherein raw material gas is introduced for oxidation into reaction tubes of a multi-tubular reactor which is equipped with, as arranged within the shell of the reactor, a plurality of reaction tubes having a catalyst packed therein and a plurality of baffle plates for changing the direction of the flow of a heating medium introduced into the shell, characterized in that the temperature of the catalyst packed in a reaction tube which is not connected with at least one baffle plate is measured, wherein the temperature and the flow rate of the heating medium to be introduced into the shell is controlled on the basis of the temperature of the catalyst measured.

2. The process according to claim 1, wherein the temperature and flow rate of the heating medium to be introduced into the shell are controlled on the basis of the temperature of the catalyst measured.

3. The process according to claim 1, wherein the temperature of the catalyst is measured at 2 to 20 points in the direction of the axis of the reaction tube.

4. The process according to claim 1, wherein the temperature of the catalyst is measured by using a multipoint thermocouple.

5. The process according to claim 1, wherein the direction of the flow of the raw material gas, which flows in the reaction tubes, and the direction of a macroscopic flow of the heating medium which flows in the shell, are the same directions.

6. The process according to claim 1, wherein a plurality of catalyst layers, which have different activities, are packed in the reaction tubes.

7. The process according to claim 1, wherein the raw material gas contains propylene, isobutylene or (meth)acrolein, as a material to be oxidized.

8. A process for catalytic vapor phase oxidation wherein raw material gas is introduced for oxidation into reaction tubes of a multi-tubular reactor which is equipped with, as arranged within the shell of the reactor, a plurality of reaction tubes having a catalyst packed therein and plurality of baffle plates for changing the direction of the flow of a heating medium introduced into the shell, characterized in that the temperature of the catalyst packed in a reaction tube which is not connected with at least one baffle plate, and the temperature of the catalyst packed in a reaction tube which is connected with all baffle plates, are measured.

9. The process according to claim 8, wherein the temperature and flow rate of the heating medium to be introduced into the shell are controlled on the basis of the temperature of the catalyst measured.

10. The process according to claim 8, wherein the temperature of the catalyst is measured at 2 to 20 points in the direction of the axis of the reaction tube.

11. The process according to claim 8, wherein the temperature of the catalyst is measured by using a multipoint thermocouple.

12. The process according to claim 8, wherein the direction of the flow of the raw material gas, which flows in the reaction tubes, and the direction of a macroscopic flow of the heating medium which flows in the shell, are the same directions.

13. The process according to claim 8, wherein a plurality of catalyst layers, which have different activities, are packed in the reaction tubes.

14. The process according to claim 8, wherein the raw material gas contains propylene, isobutylene or (meth)acrolein, as a material to be oxidized.

* * * * *